United States Patent
Sharma et al.

(10) Patent No.: US 7,666,622 B2
(45) Date of Patent: *Feb. 23, 2010

(54) MONOMERIC SELF-ASSOCIATING FUSION POLYPEPTIDES AND THERAPEUTIC USES THEREOF

(75) Inventors: Prerna Sharma, Stamford, CT (US); Margaret Karow, Putnam Valley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/582,929

(22) Filed: Oct. 18, 2006

(65) Prior Publication Data

US 2007/0087411 A1    Apr. 19, 2007

Related U.S. Application Data

(60) Provisional application No. 60/728,255, filed on Oct. 19, 2005.

(51) Int. Cl.
| | |
|---|---|
| C12P 21/06 | (2006.01) |
| C12N 15/00 | (2006.01) |
| C12N 5/00 | (2006.01) |
| C07K 14/00 | (2006.01) |
| C07H 21/04 | (2006.01) |

(52) U.S. Cl. .................. 435/69.1; 435/320.1; 435/325; 530/350; 536/23.5

(58) Field of Classification Search .................. None
See application file for complete search history.

(56) References Cited

U.S. PATENT DOCUMENTS

| 6,472,179 B2 * | 10/2002 | Stahl et al. ................. 435/69.7 |
| 6,664,227 B1 * | 12/2003 | Wynn et al. ..................... 514/8 |
| 6,793,919 B2 | 9/2004 | Mohler |
| 6,900,292 B2 | 5/2005 | Sun et al. |
| 7,083,950 B2 * | 8/2006 | Stahl et al. ................. 435/69.7 |
| 2005/0032175 A1 * | 2/2005 | Stahl et al. ................. 435/69.7 |
| 2005/0074855 A1 * | 4/2005 | Stahl et al. ................. 435/69.5 |

FOREIGN PATENT DOCUMENTS

| WO | WO 9624676 A1 * | 8/1996 |
| WO | WO 00/64944 | 2/2000 |
| WO | WO 0018932 A2 * | 4/2000 |

OTHER PUBLICATIONS

Gabay, Curr Opin Invest Drugs. May 2003;4(5):593-597, Review.*
Genbank Accession No. AF029213, Sep. 30, 1999.
Genbank Accession No. NM 000640, Feb. 25, 2007.
Genbank Accession No. NM 000877, Jul. 30, 2007.
Fountoulakis et al.; Interferon Gamma Receptor Extracellular Domain Expressed as IgG Fusion . . . ;Feb. 1995; vol. 270; pp. 3958-3964.

* cited by examiner

*Primary Examiner*—Cherie M Woodward
(74) *Attorney, Agent, or Firm*—Valeta Gregg, Esq.

(57) ABSTRACT

Monomeric fusion polypeptides comprising R1-M-L-M, wherein R1 is a target ligand-binding domain, M is a multimerizing component, and L is a linker capable of allowing one M component to interact with the other M component to form a self-associating monomer, optionally comprising a second target ligand-binding domain R2. Preferred target ligands include interleukin (IL)-13, IL-1, insulin-like growth factor (IGF)-1 and IGF-2.

12 Claims, No Drawings

MONOMERIC SELF-ASSOCIATING FUSION POLYPEPTIDES AND THERAPEUTIC USES THEREOF

CROSS-REFERENCE TO RELATED APPLICATIONS

This application claims the benefit under 35 USC §119(e) of U.S. Provisional 60/728,255 filed 19 Oct. 2005, which application is herein specifically incorporated by reference in its entirety.

BACKGROUND OF THE INVENTION

1. Field of the Invention

The invention encompasses receptor-based fusion polypeptides, as well as therapeutic uses of such polypeptides. More specifically, the invention features monomeric fusion polypeptides comprising receptor components and self-associating components.

2. Description of Related Art

In U.S. Pat. No. 6,472,179 Stahl et al. describe cytokine fusion protein fusion polypeptides capable of binding a cytokine to form a nonfunctional complex composed of two receptor components and a multimerizing component. The interleukin-13 receptor alpha component (IL-13Rα) is described, e.g., U.S. Pat. Nos. 5,710,023 and 6,248,714 (Collins et al.), which publications are herein incorporated by reference in their entireties.

BRIEF SUMMARY OF THE INVENTION

In a first aspect, the invention features a nucleic acid molecule encoding a monomeric, self-associating fusion polypeptide R1-M-L-M, wherein R1 is a target ligand-binding domain, M is a self-associating component, and L is a linker.

R1 may be one or more receptor components defining a ligand-binding domain. In a preferred embodiment, R1 is a single receptor component capable of exhibiting high affinity binding to a target ligand. In one embodiment, the receptor component binds insulin-like growth factor (IGF)-1 or IGF-2. In a preferred embodiment, the receptor component binds a cytokine selected from one of interleukin-1 (IL-1), IL-2, IL-3, IL-4, IL-5, IL-6, IL-7, IL-9, IL-11, IL-12, IL-13, IL-15, IL-16, IL-17, IL-18, IL-19, IL-20, IL-21, IL-22, IL-23, IL-24, IL-25, IL-26, IL-27, IL-30, IL-31, granulocyte macrophage colony stimulating factor, oncostatin M, G-CSF, GH, IGF-1, and leukemia inhibitory factor. In additional embodiments of the invention, the receptor component binds a cytokine which is a member of the interferon family of cytokines selected from the group consisting of IFN-gamma (IFN-γ), IFN-α, IFN-β, IL-28 and IL-29. In still further embodiments of the invention, the receptor component is capable of binding a cytokine which is a member of the TNF family of cytokines selected from the group consisting of TNF-alpha, TNF-beta, LT-beta, RANKL, CD40 ligand, Fas ligand, CD 27 ligand, CD 30 ligand, and 4-1BBL. In preferred embodiments, the receptor component binds a cytokine selected from the group consisting of IL-1, IL-10, IL-12, IL-14, IL-18, and MIF. In another embodiment the fusion partner is a ligand, such as EPO, TPO, G-SCF, GM-CSF, IL-1ra, CNTF, Axokine, GLP-1, IFNβ, IFN-A2, GH, IFG-1, IGF-2, IL-2, IFN-γ, IL-4, IL-21, IL-24, KGF, PYY, thrombin, etc.

In one embodiment of the invention, the nucleic acid molecule further encodes a second target-ligand binding domain (R2), wherein R2 is specific for the same or a different target ligand-binding component as R1. In one embodiment, the components are arranged as R1-M-L-M-R2. In another embodiment, the components are arranged as R1-R2-M-L-M.

The self-associating component (M) is any component that is capable of interacting with the second M component on the same fusion polypeptide, that is, forming an M:M structure. Preferably, the M component enhances the functionality of the fusion polypeptide. Thus, for example, a self-associating component may enhance the biological activity of the fusion polypeptide, aid in its production and/or recovery, or enhance a pharmacological property or the pharmacokinetic profile of the fusion polypeptide by, for example, enhancing its serum half-life, tissue penetrability, lack of immunogenicity, or stability.

M may be any natural or synthetic sequence capable of interacting with another self-associating component. The two M components of the fusion polypeptide of the invention will generally be the same. In specific embodiments, the self-associating component is selected from the group consisting of (i) an immunoglobulin-derived domain, (ii) an amino acid sequence between 1 to about 500 amino acids in length, comprising at least one cysteine residue, (iii) a leucine zipper, (iv) a helix loop motif, and (v) a coil-coil motif. In a more specific embodiment, the immunoglobulin-derived domain is selected from the group consisting of the Fc domain of IgG ($IgG_1$, $IgG_2$, $IgG_3$ or $IgG_4$) or the heavy chain of IgG. In one embodiment, the Fc domain of IgG is human FcΔ1(a), an Fc molecule with a mutation of the region involved in forming the disulfide bond with the light chain.

The linker L is a component which allows the multiple M components to form an intra-molecular interaction, e.g., a self-associating monomer. L may be a sequence between about 10 to about 30 amino acids in length. In a preferred embodiment, L is a sequence about 16 amino acids in length, for example the peptide of SEQ ID NO:2. In another embodiment, L is the G4S linker of SEQ ID NO:3.

The nucleic acid molecule of the invention may further optionally comprise a signal sequence (SS) component. When a SS is part of the polypeptide, any SS known to the art may be used, including synthetic or natural sequences from any source, for example, from a secreted or membrane bound protein. In one preferred embodiment, an ROR signal sequence is used (SEQ ID NO:4).

In one specific embodiment, the nucleic acid of the invention encodes a fusion protein R1-M-L-M, wherein R1 is an IL-13 receptor alpha (IL-13Rα2), M is an Fc, L is a peptide between 10-20 amino acids, and the self-associating monomeric fusion protein is capable of specifically inhibiting IL-13 activity with an $IC_{50}$ of at least $10^{-10}$ molar. More specifically, R1 is an IL-13Rα2 component amino acids 1-343 or 23-343 of SEQ ID NO:1, optionally modified with one or more of the modifications defined in modification group I.

Modification Group I: (a) amino acids 1-22 of SEQ ID NO:1 are deleted. In specific embodiments in which it may be desirable to replace the deleted amino acids with, for example, a signal sequence such as SEQ ID NO:4, thus removing Cys22 to reduce aberrant disulfide bonds formation; (b) Cys252Ile of SEQ ID NO:1; (c) an amino acid changed at position 310 of SEQ ID NO:1. In a specific embodiment, Ser310 is replaced with Cys, which may be desirable to stabilize the tertiary structure of the protein.

In another embodiment, the nucleic acid encodes a fusion protein R1-M-L-M-R2, wherein R1 is the extracellular domain of IL-1R1 and R2 is the extracellular domain of IL-1RAcP. More specifically, R1 is SEQ ID NO:13 or a fragment thereof capable of binding IL-1 and R2 is amino acids 19-333 or 1-358 of SEQ ID NO:14, and the monomeric fusion polypeptide is capable of specifically inhibiting IL-1β activity with an $IC_{50}$ of at least $10^{-10}$ molar.

In another embodiment, the nucleic acid encodes a fusion protein R1-M-L-M-R2, wherein R1 and R2 are the fragments of the extracellular domain of hIGFR. More specifically, R1 is amino acids 1-489 and R2 is amino acids 721-736 of SEQ ID NO:6, and the monomeric fusion polypeptide is capable of specifically inhibiting IGF activity with a Kd of at least $10^{-9}$ molar.

In a related second aspect, the invention features a vector comprising a nucleic acid molecule of the invention. In further third and fourth aspects, the invention encompasses vectors comprising the nucleic acid molecules of the invention, including expression vectors comprising the nucleic acid molecules operatively linked to an expression control sequence, and host-vector systems for the production of a fusion polypeptide which comprise the expression vector, in a suitable host cell; host-vector systems, wherein the suitable host cell is, without limitation, a bacterial, yeast, insect, mammalian cell or plants, such as tobacco, or animals such as cows, mice, or rabbits. Examples of suitable cells include *E. coli, B. subtilis*, BHK, COS and CHO cells. Additionally encompassed are fusion polypeptides of the invention modified by acetylation or pegylation.

In a related fifth aspect, the invention features a method of producing a fusion polypeptide of the invention, comprising culturing a host cell transfected with a vector comprising a nucleic acid molecule of the invention, under conditions suitable for expression of the fusion polypeptide from the host cell, and recovering the polypeptide so produced.

In sixth, seventh, and eighth aspects, the invention features a fusion polypeptide comprising R1-M-L-M, wherein R1, M and L are as defined above, optionally further comprising R2, as defined above. The fusion polypeptide of the invention forms an intramolecular self-association between the two M components, which association is facilitated by the L component. In a preferred embodiment, the self-associating monomeric fusion polypeptide of the invention allows R to be active, whereas an R-M alone is not, e.g., when R is IL-13Rα2. In another embodiment, the self-associating monomeric fusion polypeptide of the invention is active as an antagonist capable of binding and inhibiting a target molecule and exhibited desirable properties relative to larger prior art molecules. For example, when R1 is the extracellular domain of IL-1Racp and R2 is the extracellular domain of IL-1R1, the fusion protein R1-M-L-R2 forms a self-associating protein capable of binding and inhibiting interleukin-1 (IL-1).

In a ninth aspect, the invention features pharmaceutical compositions comprising a fusion polypeptide of the invention with a pharmaceutically acceptable carrier. Such pharmaceutical compositions may comprise a monomeric polypeptide, or nucleic acids encoding the fusion polypeptide.

The monomeric, self-associating fusion polypeptides of the invention are therapeutically useful for treating any disease or condition, which is improved, ameliorated, or inhibited by removal, inhibition, or reduction of a target ligand. For example, when the monomeric fusion polypeptide of the invention is capable of binding IL-13, the monomeric fusion polypeptide is particularly useful for the treatment of asthma, which are improved, ameliorated, or inhibited by removal, inhibition, or reduction of IL-13. Accordingly, in a further aspect, the invention features a therapeutic method for the treatment of an IL-13-related disease or condition, comprising administering a fusion polypeptide of the invention to a subject suffering from an IL-13-related disease or condition. When the monomeric, self-associating fusion polypeptide is capable of binding IL-1, the invention features a therapeutic method for the treatment of an IL-1-related condition or disease, including for example, autoinflammatory diseases such as including familial mediterranean fever (FMF), NOMID/CINCA, Muckle-Wells Syndrome, FCAS, and tumor necrosis factor receptor-associated periodic fever syndrome (TRAPS). When the monomeric, self-associating fusion polypeptide is capable of binding IGF-1 and/or IGF-2, the invention features a therapeutic method for the treatment of the IGF related conditions or disease, including for example, cancer or diabetic retinopathy. Although any mammal can be treated by the therapeutic methods of the invention, the subject is preferably a human patient suffering from or at risk of suffering from a condition or disease which can be improved, ameliorated, inhibited or treated with a fusion polypeptide of the invention.

In a further aspect, the invention further features diagnostic and prognostic methods, as well as kits for detecting, quantifying, and/or monitoring a target molecule with the monomeric fusion polypeptides of the invention.

Other objects and advantages will become apparent from a review of the ensuing detailed description.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

Definitions

The term "high affinity for" a ligand means that the fusion polypeptide of the invention binds the intended ligand with an affinity of at least $10^{-9}$ molar, preferably at least $10^{-10}$ molar, and most preferably at least $10^{-11}$ molar as determined by assay methods known in the art, for example, surface plasmon resonance analysis (e.g., BiaCore™). The term "capable of specifically blocking" or "capable of inhibiting the activity of" a target ligand means the fusion polypeptides of the invention inhibit the biological activity of the target ligand, as measured by bioassay. For example, when the target ligand is IL-13, bioassays may include luciferase-based assays using an STAT6 promoter element, and/or IL-13 stimulation of cell lines such as TF1 or of human peripheral blood cells with readouts such as growth or sCD23 secretion. When the target ligand is IL-1, bioassays may include luciferase-based assays using a NFKB promoter element, or IL-1 induced secretion of IL-6 by MRC5 cells. When the target ligand is IGF, bioassays include MCF-7 cell growth or AKT phosphorylation or binding assays (such as ELISA). "$IC_{50}$" is defined as the concentration of fusion protein required to inhibit 50% of the response to the target ligand as measured in a bioassay. The fusion polypeptides of the invention are preferably capable of inhibiting the biological activity of the target ligand with an IC50 or Kd of at least $1 \times 10^{-9}$ M, preferably $10^{-10}$ M, even more preferably $10^{-11}$ M.

A self-associating monomeric fusion polypeptide is a polypeptide possessing two associated components which form an intramolecular dimer. Thus the fusion polypeptides of the invention tend to form monomers rather than the dimers of the prior art (see, for example, U.S. Pat. No. 6,472,179 Stahl et al.).

The terms "treatment", "treating", and the like are used herein to generally mean obtaining a desired pharmacologic and/or physiological effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the invention includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a condition or disorder with an IL-13-specific fusion polypeptide, an IL-1-specific fusion polypeptide, or an IGF-specific fusion polypeptide, will encompass the treatment of a mammal, in particular, a human, who has symptoms reflective of elevated or deleterious IL-13, IL-1, or IGF, or who is expected to have such decreased activation in response to a disease, condition or treatment regimen. Treating an IL-13-related, IL-1, or IGF-related condition or disease encompasses the treatment of a human subject wherein reducing IL-13, IL-1, or IGF levels with the fusion polypeptide of the invention results in amelioration of an undesirable symptom resulting from the IL-13-related, IL-1-related or IGF-related condition or disease.

General Description

The present invention provides fusion polypeptides capable of binding a target ligand with high affinity (e.g., a Kd of at least $10^{-9}$ M) which contain two self-associating multimerizing components and form a monomeric self-dimerized polypeptide. The fusion polypeptides of the invention offer several important advantages relative to fusion polypeptides containing a single multimerizing component. For example, when the self-associating component is Fc, the monomeric fusion polypeptides of the invention retain the activity of an Fc molecule but are smaller in size than a dimer formed by two R-Fc fusion. Such monomeric fusion polypeptides may exhibit better tissue penetration, ease of production and ease of dosage formulation. Monomeric fusion polypeptides are particularly advantageous when R is human IL-13Rα2 because the IL-13Rα2-Fc dimer is inactive, whereas the inventors have found that the self-associated IL-13Rα2-Fc-L-Fc monomer is capable of binding IL-13 with high affinity, as shown below. Similarly, monomeric versions of the IL-1 trap are low affinity inhibitors of IL-1, whereas the self-associating monomer is a high affinity inhibitor of IL-1β.

Nucleic Acid Constructs and Expression

The present invention provides for the construction of nucleic acid molecules self-associating monomeric polypeptides capable of binding a target ligand with high affinity, e.g., a Kd of at least $10^{-8}$ M. As described above, the nucleic acid molecules of the invention encode self-associating fusion polypeptides capable of binding a target ligand with high affinity. Accordingly, the nucleic acid molecules may be termed "recombinant", "artificial", or "synthetic" as they are not nucleic acid molecules found in nature, e.g., not naturally occurring sequences, but are sequences constructed by recombinant DNA technology.

These nucleic acid molecules are inserted into a vector that is able to express the fusion polypeptides of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional and/or translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the beta-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase 1.

Expression vectors capable of being replicated in a bacterial or eukaryotic host comprising the nucleic acid molecules of the invention are used to transfect the host and thereby direct expression of such nucleic acids to produce the fusion polypeptides of the invention. Transfected cells may transiently or, preferably, constitutively and permanently express the polypeptides of the invention.

Self-Associating Components

The fusion polypeptides of the invention comprise two self-associating components (M) separated by a linker (L) which allows the in-line multimerizing components to interact intramolecularly. M may be any natural or synthetic sequence capable of interacting with another associating component to form a self-associating monomer. The self-associating component may be selected from the group consisting of an immunoglobulin-derived domain, a truncated multimerizing component, an amino acid sequence between 1 to about 500 amino acids in length, a leucine zipper, a helix loop motif, and a coil-coil motif. When M is a self-associating component comprising an amino acid sequence between 1 to about 500 amino acids in length, the sequence may contain one or more cysteine residues capable of forming a disulfide bond with a corresponding cysteine residue on another fusion polypeptide comprising an M with one or more cysteine residues.

In a preferred embodiment, the self-associating component comprises one or more immunoglobulin-derived domain from human IgG, IgM or IgA. In specific embodiments, the immunoglobulin-derived domain is selected from the group consisting of the Fc domain of IgG or the heavy chain of IgG. The Fc domain of IgG may be selected from the isotypes $IgG_1$, $IgG_2$, $IgG_3$, and $IgG_4$, as well as any allotype within each isotype group. In one specific embodiment, M is the Fc domain of $IgG_4$ with Ser 228 (Cabot numbering) mutated to Pro to stabilize covalent dimer formation (Mol. Immunol. (1993) 30:105-108) and/or Leu235→Glu which eliminates residual effector functions (Reddy et al. (2000) J. Immunol. 164:1925-1933). In a preferred embodiment, M is the Fc domain of $IgG_1$, or a derivative thereof which may be modified for specifically desired properties (see, for example, Armour et al. (2003) Mol. Immunol. 40:585-593; Shields et al. (2001) J. Biol. Chem. 276:6591-6604).

Linker Components

The linker L is a component which allows the multimerizing components to form an intra-molecular interaction, e.g., a self-associating (self-multimerized) monomer. Although L may be any component which functions as required above, L is preferably an amino acid sequence between about 10 to about 30 amino acids in length. In a preferred embodiment, L is a sequence about 16 amino acids in length, for example the CT peptide (CTP) of SEQ ID NO:2. In another embodiment, L is the $G_4S$ linker of SEQ ID NO:3. Other linkers may known to the art may be used, see, for example, George et al. (2003) Protein Engineering 15:871-879, herein specifically incorporated by reference.

Therapeutic Uses

The fusion polypeptides of the invention are therapeutically useful for treating any disease or condition which is improved, ameliorated, inhibited or prevented by removal, inhibition, or reduction of a target ligand. For example, in one embodiment the fusion polypeptide of the invention are capable of binding and inhibiting IL-13. IL-13 has been implicated in a variety of clinical conditions, such as eosinophil infiltration, IgE production and IL-5 production, that are characterized by a Th2 cell-driven response. Accordingly, the blocking of this responses by the fusion polypeptide will be useful for the treatment of any disease or condition in which there is increased occurrence of T-helper cells of the TH2 type.

In one embodiment, the IL-13-specific monomer of the invention is used to treat asthma. Data derived from animal experiments and examination of asthmatic humans implicate IL-13 as an initiator of the atopic condition and perpetuators of the chronic inflammatory state that typifies the asthmatic lung. IL-13 induces effects that are associated with the asthmatic phenotype, including isotype switching to IgE production, eosinophilia, mastocytosis, mucus formation, increased vascular permeability, airway hyper-responsiveness, smooth muscle hyperplasia, and subepithelial fibrosis (Hogan et al. (1997) Pharmcol. Ther. 74(3):259-283; McKenzie et al. (2000) Pharmacol. Ther. 88(2):143-151; Wills-Karp (2001) J. Allergy Clin. Immunol. 107(1):9-18).

A non-exhaustive list of specific conditions improved by inhibition or reduction of IL-13 include asthma, atopic dermatitis, immune complex disease (such as lupus, nephritis, and Graves' disease) allergic conditions, hyper IgE syndrome, immune deficiencies, idiopathic pulmonary fibrosis, hepatic fibrosis, HIV, pulmonary 'remodeling,' COPD, ulcerative colitis, cancer, Hodgkin's Lymphoma, cystic fibrosis, septic/reactive arthritis, ulcers, gastric inflammation, mucosal inflammation, Crohn's Disease, inflammatory bowel disease, dermatitis herpetiformis, chronic idiopathic urticaria, scleroderma, hypertrophic scarring, Whipple's Disease, benign prostate hyperplasia, lung allergic reactions to medication, Kawasaki disease, sickle cell disease (including sickle cell crisis), Churg-Strauss syndrome, pre-eclampsia, Sjögren's syndrome, autoimmune lymphoproliferative syndrome, autoimmune hemolytic anemia, Barrett's esophagus, autoimmune uveitis, tuberculosis, and nephrosis, adjuvants to allergy immunotherapy and as vaccine adjuvants, and myasthenia gravis, bullous pemphigoid, transplant and graft vs host disease, viral, parasitic, bacterial disease, and fungal infection. (U.S. Pat. No. 6,328,954; Idzerda, R. J. et al. 1990 J Exp. Med. 171:861-873).

The invention further provides a monomeric, self-associating fusion protein capable of binding interleukin-1 (IL-1) with high affinity. Conditions effectively treated by an IL-1 inhibitor or pharmaceutical composition described herein include pulmonary diseases such as asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, broncho-pulmonary dysplasia (BPD); chronic obstructive pulmonary diseases (e.g. emphysema and chronic bronchitis) occupational lung diseases, bronchiolit-erans organizing pneumonia, pulmonary fibrosis, including idiopathic pulmonary fibrosis and radiation-induced pulmonary fibrosis; pulmonary sarcoidosis; and allergies, including allergic rhinitis, contact dermatitis, atopic dermatitis, asthma, asbestosis, coal worker's pneumoconiosis, silicosis or similar conditions associated with long-term exposure to fine particles, and chronic fibrotic lung disease of preterm infants, and ARDS, all of which may be treated with combinations of an IL-1 inhibitor and an IL-4 inhibitor and/or IL-13 inhibitor, e.g. IL-4/13 trap, IL-4R antibody that inhibits IL-13 and IL-4 activity, an anti-IL-13 antibody, or IL-13Ra2-Fc-CTP-Fc.

Such combinations are useful also for treating patients suffering from various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid. Other diseases treatable with the combination of an IL-1 inhibitor and an IL-4 and/or IL-13 inhibitor include myesthenia gravis, sarcoidosis, including pulmonary sarcoidosis, scleroderma, reactive arthritis, hyper IgE syndrome, multiple sclerosis and idiopathic hypereosinophil syndrome. The combination is used also for treating allergic reactions to medication and as an adjuvant to allergy immunotherapy.

The IL-1R inhibitor and pharmaceutical compositions described herein are useful for treating protozoal diseases, including malaria and schistosomiasis and to treat erythema nodosum leprosum; bacterial or viral meningitis; tuberculosis, including pulmonary tuberculosis; and pneumonitis secondary to a bacterial or viral infection including influenza infection and infectious mononucleosis. Cardiovascular disorders and injuries are treatable and/or preventable with disclosed either pharmaceutical compositions or IL-1 inhibitors alone or in combination with other cytokine inhibitors. Cardiovascular disorders treatable include aortic aneurysms; including abdominal aortic aneurysms, acute coronary syndrome, arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure, congestive heart failure, cachexia of heart failure; myocardial infarction; restenosis and/or atherosclerosis after heart surgery or after carotid artery balloon angioplastic procedures; silent myocardial ischemia; left ventricular pump dysfunction, post implantation complications of left ventricular assist devices; Raynaud's phenomena; thrombophlebitis; vasculitis, including Kawasaki's vasculitis; veno-occlusive disease, giant cell arteritis, Wegener's granulomatosis; mental confusion following cardio pulmonary by pass surgery, and Schoenlein-Henoch purpura.

Also provided herein are methods for using IL-1 inhibitors of the invention, compositions, and combination therapies to treat various hematologic and oncologic disorders. For example, IL-1 inhibitors, alone or in combination with other cytokine inhibitors or other active agents as described above, can be used to treat various forms of cancer, including acute myelogenous leukemia, chronic myelogenous leukemia leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Solid tumors, including sarcoma, osteosarcoma, and carcinoma, such as adenocarcinoma (for example, breast cancer) and squamous cell carcinoma are also treatable. Additional treatable cancers include esophogeal cancer, gastric cancer, gall bladder carcinoma, leukemia, including acute myelogenous leukemia, chronic myelogenous leukemia, myeloid leukemia, chronic or acute lymphoblastic leukemia and hairy cell leukemia. Other malignancies with invasive metastatic potential, including multiple myeloma, can be treated with the subject compounds, compositions and combination therapies.

In addition, the disclosed IL-1 inhibitors can be used to treat anemias and hematologic disorders, including chronic idiopathic neutropenia, anemia of chronic disease, aplastic anemia, including Fanconi's aplastic anemia; idiopathic thrombocytopenic purpura (ITP); thrombotic thrombocytopenic purpura, myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Various lymphoproliferative disorders also are treatable with IL-1 inhibitors of the invention, including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sezary syndrome.

Non-arthritic disorders of the bones and joints and also treatable with the constructs and compositions described herein. This encompasses osteoclast disorders that lead to bone loss, such as but not limited to osteoporosis, including post-menopausal osteoporosis, osteoarthritis, periodontitis resulting in tooth loosening or loss, and prosthesis loosening after joint replacement (generally associated with an inflammatory response to wear debris). This latter condition also is called "orthopedic implant osteolysis." Another condition treatable with the compounds, compositions and combination therapies of the invention is temporal mandibular joint dysfunction (TMJ).

The IL-1 inhibitors or pharmaceutical compositions of the invention can also be used to treat rheumatic disorders including adult and juvenile rheumatoid arthritis; scleroderma; systemic lupus erythematosus; gout; osteoarthritis; polymyalgia rheumatica; seronegative spondylarthropathies, including ankylosing spondylitis, and Reiter's disease, psoriatic arthritis and chronic Lyme arthritis. The antibodies of this invention are also useful for treating inflammation of the voluntary muscle and other muscles, including dermatomyositis, inclusion body myositis, polymyositis, and lymphangioleimyomatosis.

Another use for the constructs and pharmaceutical compositions of the invention is the treatment and/or prevention of primary amyloidosis and the secondary amyloidosis that is characteristic of various condition including Alzheimer's disease, secondary reactive amyloidosis; Down's syndrome; and dialysis-associated amyloidosis. Also treatable with the pharmaceutical compositions of the invention are inherited periodic fever syndromes, including familial Mediterranean fever, hyperimmunoglobulin D and periodic fever syndrome and TNF-receptor associated periodic syndromes (TRAPS).

The IL-1-targeting fusion protein of the invention may be used in the treatment of IL-1 related diseases or condition, such as autoinflammatory disorders. One important group of autoinflammatory disorders encompasses autosomal dominant conditions associated with mutations in CIAS-1, a gene that encodes a pyrin-related protein called "cryopyrin" (Feldmann et al. (2002) Am. J. Hum. Genet. 71:198-203; Hoffman et al. (2001) Nat. Genet. 29:301-305). These disorders include Neonatal Onset Multisystem Inflammatory Disorder (NOMID/CINCA), Muckle-Wells Syndrome (MWS), and Familial Cold Autoinflammatory Syndrome (FCAS). Another condition which may be treated is FMF, a recessively inherited condition characterized by episodes of fever and serositis or synovitis; some subjects also develop systemic amyloidosis (Balow et al. (1997) Genomics 44:280-291). The IL-1 inhibitors of the invention may also be used to treat Still's Disease (systemic onset juvenile idiopathic arthritis), is manifest by spiking fevers, evanescent salmon color rash, arthritis, arthralgia, and hepatosplenomegaly (Masson et al. (1995) Rev. Rhum. Engl. Ed. 62:748-757; Spiegel et al. (2000) Arthritis Rheum. 43:2402-2409). Other diseases that have also been considered autoinflammatory include Kawasaki disease, Blau's syndrome, Early Onset Sarcoidosis (EOS), granulomatosis, arthritis and uveitis., Hidradenitis suppurativa, Behcet's, hyperimmunoglobulinaemia D with periodic fever syndrome (HIDS), tumour necrosis factor receptor-associated periodic fever syndrome (TRAPS), and Pyogenic sterile arthritis, pyoderma gangrenosum and acne (PAPA syndrome). IGF-I and IGF II are involved in a number of pathophysiological conditions, including tumorigenesis, and high serum blood levels of IGF-I/IGF-II are associated with risk for development of breast, prostate, colon and lung cancer (LeRoith et al. (2003) Cancer Lett. 195:127-137). In diabetic retinopathy, atherosclerosis and restenosis there is elevated levels of IGF1 and IGF II (Angard et al Artery (1991) 18:197-225; Forrester et al. (1991) Am J Cardiology 68:24C-33C.)

Suitable Subject for Treatment

In one embodiment, a suitable subject for treatment is a human diagnosed as suffering from specific conditions improved by inhibition or reduction of IL-13 include atopic dermatitis, immune complex disease (such as lupus, nephritis, and Grave's disease) allergic conditions, hyper IgE syndrome, immune deficiencies, idiopathic pulmonary fibrosis, hepatic fibrosis, HIV, pulmonary 'remodeling', COPD, ulcerative colitis, cancer, Hodgkin's Lymphoma, bullous pemphigoid, transplant and graft vs host disease viral, parasitic, bacterial disease and fungal infection.

In another embodiment, a suitable subject for treatment is a human diagnosed as suffering from a condition which is improved, ameliorated, or inhibited with an IL-1 antagonist, such as familial mediterranean fever (FMF), NOMID/CINCA, Muckle-Wells Syndrome, FCAS, and tumour necrosis factor receptor-associated periodic fever syndrome (TRAPS).

Combination Therapies

In numerous embodiments, the fusion polypeptides of the invention may be administered in combination with one or more additional compounds or therapies. In a preferred embodiment, an IL-13-specific monomer of the invention is co-administered with an agent capable of inhibiting IL-4, such as an anti-IL-4 antibody or an IL-4 mutein. Other combinations include, short-acting inhaled beta2 agonists, oral beta2 agonists, inhaled anticholinergics, oral corticosteroids, inhaled corticosteroids, cromolyn sodium (GASTROCROM™, Celltech), nedocromil, long-acting beta2 agonists, leukotriene modifiers, theophylline, calcinerin inhibitors, picrolimus, sirolimus, anti-IgE (Zolair. Genentech), NFKB inhibitors, p38 MAP kinase inhibitors (VX-702), ICE inhibitors (VX-765), IL-1 inhibitors (IL-1 trap, Regeneron; KINERET™, Amgen), TNFa inhibitors (REMICADE™, Centocor; ENBREL™, Amgen; HUMIRA™, Abbott), IL-5 inhibitors, IL-18 inhibitors, IFN-γ inhibitors, IFN-α blockers. For example, multiple fusion polypeptides can be co-administered, or one or polypeptide can be administered in conjunction with one or more therapeutic compounds. A benefit of the combined use of the fusion polypeptide of the invention with a second therapeutic agent is that it provides improved efficacy and/or reduced toxicity of either therapeutic agent.

In specific embodiments of the therapeutic method of the invention, the subject is treated with a combination of a first IL-1-binding fusion protein trap molecule and a second therapeutic agent. The second therapeutic agent may be a second IL-1 antagonist, such as, for example, a second IL-1-binding fusion protein trap, anakinra (KINERET™, Amgen), a recombinant, nonglycosylated form of the human IL-1 receptor antagonist (IL1Ra), or an anti-IL-18 drug such as IL-18BP or a derivative, an IL-18-binding fusion protein trap (an "IL-18 trap"), anti-IL-18, anti-IL-18R1, or anti-IL-18RAcp antibodies or antibody fragments. Other co-therapies include low dose colchine for FMF, aspirin or other NSAIDs, steroids such as prednisolone, methotrexate, low dose cyclosporine A, TNF inhibitors such as Enbrel®, or Humira®, other inflammatory inhibitors such as inhibitors of caspase-1, p38, IKK1/2, CTLA-4Ig, anti-IL-6 or anti-IL6Ra, etc.

Methods of Administration

The invention provides methods of treatment comprising administering to a subject an effective amount of a fusion polypeptide of the invention. In a preferred aspect, the fusion polypeptide is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intra-articular, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination. Systemic expression may also be achieved by plasmid injection (intradermally or intramuscularly) and electroporation into cells.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

In one embodiment, the pharmaceutical composition of the invention is a sustained release composition. Sustained release formulations for delivery of biologically active peptides are known to the art. For example, U.S. Pat. No. 6,740,634, herein specifically incorporated by reference in its entirety, describes a sustained-release formulation containing a hydroxynaphtoic acid salt of a biologically active substance and a biodegradable polymer. U.S. Pat. No. 6,699,500, herein specifically incorporated by reference in its entirety, discloses a sustained-release formulation capable of releasing a physiologically active substance over a period of at least 5 months.

Pharmaceutical Compositions

The present invention also provides pharmaceutical compositions comprising a fusion polypeptide of the invention. Such compositions comprise a therapeutically effective amount of one or more fusion polypeptide(s), and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The fusion polypeptide of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the fusion polypeptide that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 0.02-10 milligrams active compound per kilogram body weight.

Cellular Transfection and Gene Therapy

The present invention encompasses the use of nucleic acids encoding the fusion polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell facilitated by lipid mixes or electroporation. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing levels of a target ligand in a human or other animal comprising transfecting a cell with a nucleic acid encoding a polypeptide of the invention, wherein the nucleic acid comprises an inducible promoter operably linked to the nucleic acid encoding the polypeptide. For gene therapy procedures in the treatment or prevention of human disease, see for example, Van Brunt (1998) Biotechnology 6:1149-1154.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Self-Assembling Fusion Polypeptides

Using methods known to the art, monomeric IL-1-specific fusion polypeptides were generated with a His tag, comprising hIL-1RAcp (SEQ ID NO:14), hIL-1RAcp.hIL-1R1myc.myc.His6 (SEQ ID NO:12) or monomeric self-associating fusion polypeptide such as hIL-1RAcp.hIL-1R1.TG.hFc.ARA.CTP.TG.hFc (SEQ ID NO:11), hIL-1RAcp.hIL-1R1.hFc (SEQ ID NO:17), and hIL-1R1.hFc.hIL-1RAcp (SEQ ID NO:9). A second set of IL-13-specific molecules were generated: hIL-13Rα2.hFc (SEQ ID NO:15) and hIL-13Rα2.hFc.CTP.hFc (SEQ ID NO:16). A third set of IGF specific molecules were generated hIGF1R (1-489).hFc.CTP.hFc.CTP (SEQ ID NO:8) and hIGFR(1-489).hFc.CTP (SEQ ID NO:7).

Example 2

In Vitro Bioactivity of Fusion Polypeptides

Self-associating polypeptides were produce as small-scale supernatants by transiently transfecting CHO cells, using Lipofectamine/LIPO plus (Life Technologies), with DNA constructs encoding the proteins. Supernatants were collected after 72 hours and protein expression was measured by Western blotting with anti-human Fc or antibodies against human IL-13ra2 or IL-1R1 HRP-conjugated antibody (Promega) and visualized by ECL (Pierce). Briefly, $5.4 \times 10^5$ CHOK1 cells per well of a 6 well tissue culture dish were transfected using 1 μg of DNA and 5 μl of lipofectamine in OptiMEM™ (Gibco). After 12 h the cells were washed with OptiMEM™ and 2 ml of CHO serum free medium (Gibco) was added. After 60 h and 72 h the media was collected and centrifuged to remove cellular debris and 5 μl of the supernatant was run on a 4-12% Tris Glycine SDS PAGE gel under reducing conditions. The proteins were then transferred to PVDF membranes using standard western blot procedures and incubated with horseradish peroxidase conjugated antibody against human Fc, IL-13Ra2 or IL-1R1, visualized with ECL, and quantified. Bioactivities of the fusion polypeptides generated in Example 1 were tested as follows:

TF1 Bioassay. TF1 cells that had been stably transfected with hIL-13Rα1 were maintained in growth media (10 ng/ml GM-CSF, RPMI 1640, 10% FBS, L-glutamine, penicillin, Streptomycin). For the bioassay, cells are washed 3 times in assay media (as above but without GM-CSF) and then plated at $2 \times 10^4$ cells in 50 μl of assay media. The purified fusion polypeptides were serially diluted into assay media. 25 ul of each of the 13 fusion polypeptides was added to the cells. 25 μl of either IL-13 (15 pM) was then added to the wells containing the cells and the fusion polypeptides. Cells were then incubated at 37° C., 5% $CO_2$ for ~70 hrs. The extent of TF1 cell proliferation was measured by the CCK-8 assay according to the manufacturer's protocol (Dojindo Laboratories). The results are shown in Table 1 below.

IL-1 Bioassay. The HEK293/NFκB-luciferase bioassay is used to determine the ability of the IL-1-specific polypeptides of the invention to block the activity of human IL-1 (hIL-1). Human embryonic kidney 293, HEK293, cells, were transfected with an NFκB-luciferase reporter plasmid. By placing an NFκB promoter element upstream of the luciferase gene one can monitor NFκB activity in cells. Because IL-1 signaling is mediated by NFκB, when cells containing the 293/NFκB luciferase construct the luciferase gene is expressed and luciferase activity can be detected in cell lysates. A stable, transfected, cell line, HEK293/D9, was selected for good response to IL-1β as detected by luciferase activity.

For the assay, NFκB-Luciferase cells were suspended at $1.25 \times 10^5$ cells per ml in medium and 0.08 ml of cells plated (10,000 cells per well) into the wells of a 96 well tissue culture plate. Plates were incubated for ~16 hours at 37° C. in a humidified 5% $CO_2$ incubator. hIL-1-specific polypeptides and recombinant human IL-1β at varying doses were separately mixed in a 96 well tissue culture dish. 0.026 ml of each of these mixtures were then added to the 96 well plate (hIL-1-specific polypeptides added first) containing the NFκB-Luciferase cells such that the final concentration of IL-1β is 4 pM and the final concentrations of the hIL-1-specific self associating polypeptides ranged from 0.017 pM to 30 nM. Control wells contain no hIL-1-specific polypeptide. Plates were incubated at 37° C. for 6 hours in a humidified 5% $CO_2$ incubator. After 6 hours, the plates were equilibrated to room temperature for ~30 minutes and 130 µl of Steady-Glo™ luciferase substrate (Promega) was added. Plates were incubated at room temperature for ~10 minutes and then read on a Victor multilabel counter (Luminescence 1 sec/well). IC50s were measured which is a 50% reduction in IL-1 stimulated activity, then determined with a 4 parameter fit analysis using Prism software from Graph Pad™.

In vitro binding activity of the fusion polypeptides. Wells were coated with 2 ug/ml of anti-hFc antibody (Pierce) overnight at 4° C. and blocked with PBS with 05% Tween and 10% BSA (PBST). IGF trap molecules were added at different dilutions. After 1 hr at room temperature, the wells were washed 4x with PBST and biotinylated IGF-1 (GroPep) added at 1 ug/ml. Streptavidin HRP (0.2 ug/ml) in PBST was added and developed for 20 min. Kd was determined using standard techniques using Prism software from Graph Pad™.

TABLE 1

| Fusion Polypeptide | KD | IC$_{50}$ pM |
|---|---|---|
| hIL-1RAcp.hIL-1R1.myc.myc.His6 (SEQ ID NO: 12) | | 3400 |
| hIL-1RI.TG.hFc.ARA.CTP.TG.hFc.ARA.hIL-1RAcP (SEQ ID NO: 10) | | 23 |

TABLE 1-continued

| Fusion Polypeptide | KD | IC$_{50}$ pM |
|---|---|---|
| hIL-1RAcp.hIL-1R1 TG.hFc.ARA.CTP.TG.hFc (SEQ ID NO: 11) | | 100 |
| hIL-13Rα2.hFc (SEQ ID NO: 15) | | not active |
| hIL-13Rα2.hFc.CTP.hFc (SEQ ID NO: 16) | | Active |
| hIGFR (1-489).hFc.CT (SEQ ID NO: 7) | $1 \times 10^{-9}$ M | |
| hIGFR (1-489).hFc.CT.hFc.CT (SEQ ID NO: 8) | $2 \times 10^{-9}$ M | |

In order to analyze the expression of the self associated hFc ILI trap, constructs hILIRAcp.hILIR1 (SEQ ID NO:17), hIL-1R1.hFc.hILIRAcp (SEQ ID NO:9), hIL-IRI.TG.hFc.ARA.CTP.TG.hFc.ARA.hIL-IRAcp (SEQ ID NO:10) were expressed in CHOK1 cells. CHOK1 cells were maintained in Ham's F-12 with 10% FBS. Lipofectamine (Gibco) was used to transfect these constructs into CHOK1 cells using standard transient transfection procedures. $5.4 \times 10^5$ CHOK1 cells per well of a 6 well tissue culture dish were transfected using 1 µg of DNA and 5 µl of lipofectamine in optiMEM™ (Gibco). After 12 h the cells were washed with optiMEM and 2 ml of CHO serum free medium (Gibco) was added. After 60 h and 72 h, the media was collected and centrifuged to remove cellular debris and 5 µl of the supernatant was run on a 4-12% Tris Glycine SDS PAGE gel under nonreducing conditions. The proteins were then transferred to PVDF membranes using standard western blot procedures and incubated with horse radish peroxidase conjugated antibody against human Fc (Lane 1=hILIRI.hILIRAcp.hFc (SEQ ID NO:5); lane 2=hILIR1.hFc.hILIRAcp (SEQ ID NO:9); lane 3=hILR1.hFc.CTP.hFc.hILIRAcP (SEQ ID NO:10)). The results showed that hILIRI.hILIRAcp.hFc (SEQ ID NO:5) and hILIRa.hFc.hILIRAcp both ran at >300 kDa, whereas is hILIRa.hFc.CTP.hFc.hILIRAcP (SEQ ID NO:10) ran at approximately 180 kDa, indicating the hFc are self associating rather than dimerizing as observed in the previous two constructs.

We claim:

1. A nucleic acid encoding monomeric fusion polypeptide R1-M-L-M, wherein R1 is a ligand-binding domain of an interleukin receptor capable of binding an interleukin target ligand, M is a self-associating component, and L is a linker, wherein the nucleic acid encodes a fusion polypeptide comprising the amino acid sequence of SEQ ID NO:16.

2. A nucleic acid encoding monomeric fusion polypeptide R1-M-L-M, wherein R1 is a first ligand-binding domain of an interleukin receptor capable of binding an interleukin target ligand, M is a self-associating component, L is a linker, and further comprising R2, wherein R2 is a second ligand-binding domain of an interleukin receptor which is capable of binding an interleukin target ligand that is the same or different from the interleukin target ligand of R1, wherein the nucleic acid encodes a fusion polypeptide comprising the amino acid sequence of SEQ ID NO:10 or SEQ ID NO: 11.

3. A vector comprising the nucleic acid of claim 1.

4. A host-vector system for the production of a fusion polypeptide comprising the vector of claim 3 in a suitable host cell.

5. The host vector system of claim 4, wherein the cell is a *E. coil, B. subtilis*, BHK, COS or CHO cell.

6. A method of producing a fusion polypeptide, comprising growing the cells of the host-vector system of claim 4 under conditions permitting production of the fusion polypeptide and recovering the fusion polypeptide so produced.

7. A monomeric fusion polypeptide R1-M-L-M, wherein R1 is a ligand-binding domain of an interleukin receptor capable of binding an interleukin target ligand, M is a self-associating component, and L is a linker, comprising the amino acid sequence of SEQ ID NO:16.

8. A monomeric fusion polypeptide R1-M-L-M further comprising R2, wherein R1 is a first ligand-binding domain of an interleukin receptor capable of binding an interleukin target ligand, R2 is a second ligand-binding domain of an interleukin receptor capable of binding an interleukin target ligand, M is a self-associating component, and L is a linker, comprising the amino acid sequence of SEQ ID NO:10 or SEQ ID NO:11.

9. A vector comprising the nucleic acid molecule of claim 2.

10. A host-vector system for the production of a fusion polypeptide comprising the vector of claim 9 in a suitable host cell.

11. The host vector system of claim 10, wherein the cell is a *E. coil, B. subtilis*, BHK, GOS or CHO cell.

12. A method of producing a fusion polypeptide, comprising growing the cells of the host-vector system of claim 10 under conditions permitting production of the fusion polypeptide and recovering the fusion polypeptide so produced.

* * * * *

SEQUENCE LISTING

```
<160> NUMBER OF SEQ ID NOS: 17

<210> SEQ ID NO 1
<211> LENGTH: 380
<212> TYPE: PRT
<213> ORGANISM: Homo sapiens

<400> SEQUENCE: 1

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
```

-continued

```
                    20                  25                  30
Asn Pro Pro Gln Asp Phe Glu Ile Val Asp Pro Gly Tyr Leu Gly Tyr
             35                  40                  45
Leu Tyr Leu Gln Trp Gln Pro Pro Leu Ser Leu Asp His Phe Lys Glu
 50                  55                  60
Cys Thr Val Glu Tyr Glu Leu Lys Tyr Arg Asn Ile Gly Ser Glu Thr
 65                  70                  75                  80
Trp Lys Thr Ile Ile Thr Lys Asn Leu His Tyr Lys Asp Gly Phe Asp
                     85                  90                  95
Leu Asn Lys Gly Ile Glu Ala Lys Ile His Thr Leu Leu Pro Trp Gln
            100                 105                 110
Cys Thr Asn Gly Ser Glu Val Gln Ser Ser Trp Ala Glu Thr Thr Tyr
            115                 120                 125
Trp Ile Ser Pro Gln Gly Ile Pro Glu Thr Lys Val Gln Asp Met Asp
            130                 135                 140
Cys Val Tyr Tyr Asn Trp Gln Tyr Leu Leu Cys Ser Trp Lys Pro Gly
145                 150                 155                 160
Ile Gly Val Leu Leu Asp Thr Asn Tyr Asn Leu Phe Tyr Trp Tyr Glu
                165                 170                 175
Gly Leu Asp His Ala Leu Gln Cys Val Asp Tyr Ile Lys Ala Asp Gly
            180                 185                 190
Gln Asn Ile Gly Cys Arg Phe Pro Tyr Leu Glu Ala Ser Asp Tyr Lys
            195                 200                 205
Asp Phe Tyr Ile Cys Val Asn Gly Ser Ser Glu Asn Lys Pro Ile Arg
210                 215                 220
Ser Ser Tyr Phe Thr Phe Gln Leu Gln Asn Ile Val Lys Pro Leu Pro
225                 230                 235                 240
Pro Val Tyr Leu Thr Phe Thr Arg Glu Ser Ser Cys Glu Ile Lys Leu
                245                 250                 255
Lys Trp Ser Ile Pro Leu Gly Pro Ile Pro Ala Arg Cys Phe Asp Tyr
                260                 265                 270
Glu Ile Glu Ile Arg Glu Asp Asp Thr Thr Leu Val Thr Ala Thr Val
            275                 280                 285
Glu Asn Glu Thr Tyr Thr Leu Lys Thr Thr Asn Glu Thr Arg Gln Leu
            290                 295                 300
Cys Phe Val Val Arg Ser Lys Val Asn Ile Tyr Cys Ser Asp Asp Gly
305                 310                 315                 320
Ile Trp Ser Glu Trp Ser Asp Lys Gln Cys Trp Glu Gly Glu Asp Leu
                325                 330                 335
Ser Lys Lys Thr Leu Leu Arg Phe Trp Leu Pro Phe Gly Phe Ile Leu
            340                 345                 350
Ile Leu Val Ile Phe Val Thr Gly Leu Leu Leu Arg Lys Pro Asn Thr
            355                 360                 365
Tyr Pro Lys Met Ile Pro Glu Phe Phe Cys Asp Thr
            370                 375                 380
```

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Val Phe Glu Asn Phe Leu His Asn Ser Ile Phe Val Pro Arg Pro Glu

-continued

```
1               5               10              15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

```
Gly Gly Gly Gly Ser Gly Gly Gly Ser Gly Gly Gly Gly Ser
1               5                   10                  15
```

<210> SEQ ID NO 4
<211> LENGTH: 29
<212> TYPE: PRT
<213> ORGANISM: Homo sapiens

<400> SEQUENCE: 4

```
Met His Arg Pro Arg Arg Arg Gly Thr Arg Pro Pro Leu Ala Leu
1               5                   10                  15

Leu Ala Leu Leu Leu Ala Ala Arg Gly Ala Asp Ala
            20                  25
```

<210> SEQ ID NO 5
<211> LENGTH: 903
<212> TYPE: PRT
<213> ORGANISM: Artificial Sequence
<220> FEATURE:
<223> OTHER INFORMATION: Synthetic

<400> SEQUENCE: 5

```
Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
```

-continued

```
            210                 215                 220
Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ala Arg Ala Ser
                325                 330                 335

Glu Arg Cys Asp Asp Trp Gly Leu Asp Thr Met Arg Gln Ile Gln Val
            340                 345                 350

Phe Glu Asp Glu Pro Ala Arg Ile Lys Cys Pro Leu Phe Glu His Phe
        355                 360                 365

Leu Lys Phe Asn Tyr Ser Thr Ala His Ser Ala Gly Leu Thr Leu Ile
370                 375                 380

Trp Tyr Trp Thr Arg Gln Asp Arg Asp Leu Glu Pro Ile Asn Phe
385                 390                 395                 400

Arg Leu Pro Glu Asn Arg Ile Ser Lys Glu Lys Asp Val Leu Trp Phe
                405                 410                 415

Arg Pro Thr Leu Leu Asn Asp Thr Gly Asn Tyr Thr Cys Met Leu Arg
            420                 425                 430

Asn Thr Thr Tyr Cys Ser Lys Val Ala Phe Pro Leu Glu Val Val Gln
        435                 440                 445

Lys Asp Ser Cys Phe Asn Ser Pro Met Lys Leu Pro Val His Lys Leu
450                 455                 460

Tyr Ile Glu Tyr Gly Ile Gln Arg Ile Thr Cys Pro Asn Val Asp Gly
465                 470                 475                 480

Tyr Phe Pro Ser Ser Val Lys Pro Thr Ile Thr Trp Tyr Met Gly Cys
                485                 490                 495

Tyr Lys Ile Gln Asn Phe Asn Asn Val Ile Pro Glu Gly Met Asn Leu
            500                 505                 510

Ser Phe Leu Ile Ala Leu Ile Ser Asn Asn Gly Asn Tyr Thr Cys Val
        515                 520                 525

Val Thr Tyr Pro Glu Asn Gly Arg Thr Phe His Leu Thr Arg Thr Leu
530                 535                 540

Thr Val Lys Val Val Gly Ser Pro Lys Asn Ala Val Pro Pro Val Ile
545                 550                 555                 560

His Ser Pro Asn Asp His Val Val Tyr Glu Lys Glu Pro Gly Glu Glu
                565                 570                 575

Leu Leu Ile Pro Cys Thr Val Tyr Phe Ser Phe Leu Met Asp Ser Arg
            580                 585                 590

Asn Glu Val Trp Trp Thr Ile Asp Gly Lys Lys Pro Asp Asp Ile Thr
        595                 600                 605

Ile Asp Val Thr Ile Asn Glu Ser Ile Ser His Ser Arg Thr Glu Asp
610                 615                 620

Glu Thr Arg Thr Gln Ile Leu Ser Ile Lys Lys Val Thr Ser Glu Asp
625                 630                 635                 640
```

```
Leu Lys Arg Ser Tyr Val Cys His Ala Arg Ser Ala Lys Gly Glu Val
                645                 650                 655

Ala Lys Ala Ala Lys Val Lys Gln Lys Val Pro Ala Pro Arg Tyr Thr
            660                 665                 670

Val Glu Thr Gly Asp Lys Thr His Thr Cys Pro Pro Cys Pro Ala Pro
        675                 680                 685

Glu Leu Leu Gly Gly Pro Ser Val Phe Leu Phe Pro Pro Lys Pro Lys
    690                 695                 700

Asp Thr Leu Met Ile Ser Arg Thr Pro Glu Val Thr Cys Val Val Val
705                 710                 715                 720

Asp Val Ser His Glu Asp Pro Glu Val Lys Phe Asn Trp Tyr Val Asp
                725                 730                 735

Gly Val Glu Val His Asn Ala Lys Thr Lys Pro Arg Glu Glu Gln Tyr
            740                 745                 750

Asn Ser Thr Tyr Arg Val Val Ser Val Leu Thr Val Leu His Gln Asp
        755                 760                 765

Trp Leu Asn Gly Lys Glu Tyr Lys Cys Lys Val Ser Asn Lys Ala Leu
    770                 775                 780

Pro Ala Pro Ile Glu Lys Thr Ile Ser Lys Ala Lys Gly Gln Pro Arg
785                 790                 795                 800

Glu Pro Gln Val Tyr Thr Leu Pro Pro Ser Arg Asp Glu Leu Thr Lys
                805                 810                 815

Asn Gln Val Ser Leu Thr Cys Leu Val Lys Gly Phe Tyr Pro Ser Asp
            820                 825                 830

Ile Ala Val Glu Trp Glu Ser Asn Gly Gln Pro Glu Asn Asn Tyr Lys
        835                 840                 845

Thr Thr Pro Pro Val Leu Asp Ser Asp Gly Ser Phe Phe Leu Tyr Ser
    850                 855                 860

Lys Leu Thr Val Asp Lys Ser Arg Trp Gln Gln Gly Asn Val Phe Ser
865                 870                 875                 880

Cys Ser Val Met His Glu Ala Leu His Asn His Tyr Thr Gln Lys Ser
                885                 890                 895

Leu Ser Leu Ser Pro Gly Lys
            900

<210> SEQ ID NO 6
<211> LENGTH: 736
<212> TYPE: PRT
<213> ORGANISM: Homo sapiens

<400> SEQUENCE: 6

Met Lys Ser Gly Ser Gly Gly Gly Ser Pro Thr Ser Leu Trp Gly Leu
 1               5                  10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
```

-continued

```
            100                 105                 110
Tyr Asn Tyr Ala Leu Val Ile Phe Glu Met Thr Asn Leu Lys Asp Ile
            115                 120                 125
Gly Leu Tyr Asn Leu Arg Asn Ile Thr Arg Gly Ala Ile Arg Ile Glu
            130                 135             140
Lys Asn Ala Asp Leu Cys Tyr Leu Ser Thr Val Asp Trp Ser Leu Ile
145                 150                 155                 160
Leu Asp Ala Val Ser Asn Asn Tyr Ile Val Gly Asn Lys Pro Pro Lys
                    165                 170                 175
Glu Cys Gly Asp Leu Cys Pro Gly Thr Met Glu Glu Lys Pro Met Cys
                180                 185                 190
Glu Lys Thr Thr Ile Asn Asn Glu Tyr Asn Tyr Arg Cys Trp Thr Thr
            195                 200                 205
Asn Arg Cys Gln Lys Met Cys Pro Ser Thr Cys Gly Lys Arg Ala Cys
            210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                    245                 250                 255
Ala Gly Val Cys Val Pro Ala Cys Pro Pro Asn Thr Tyr Arg Phe Glu
                260                 265                 270
Gly Trp Arg Cys Val Asp Arg Asp Phe Cys Ala Asn Ile Leu Ser Ala
            275                 280                 285
Glu Ser Ser Asp Ser Glu Gly Phe Val Ile His Asp Gly Glu Cys Met
            290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Glu Lys
                    325                 330                 335
Lys Thr Lys Thr Ile Asp Ser Val Thr Ser Ala Gln Met Leu Gln Gly
                340                 345                 350
Cys Thr Ile Phe Lys Gly Asn Leu Leu Ile Asn Ile Arg Arg Gly Asn
            355                 360                 365
Asn Ile Ala Ser Glu Leu Glu Asn Phe Met Gly Leu Ile Glu Val Val
            370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                    405                 410                 415
Asn Tyr Ser Phe Tyr Val Leu Asp Asn Gln Asn Leu Gln Gln Leu Trp
                420                 425                 430
Asp Trp Asp His Arg Asn Leu Thr Ile Lys Ala Gly Lys Met Tyr Phe
            435                 440                 445
Ala Phe Asn Pro Lys Leu Cys Val Ser Glu Ile Tyr Arg Met Glu Glu
            450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Ser Asp Val Leu His Phe Thr
                    485                 490                 495
Ser Thr Thr Thr Ser Lys Asn Arg Ile Ile Ile Thr Trp His Arg Tyr
                500                 505                 510
Arg Pro Pro Asp Tyr Arg Asp Leu Ile Ser Phe Thr Val Tyr Tyr Lys
            515                 520                 525
```

```
Glu Ala Pro Phe Lys Asn Val Thr Glu Tyr Asp Gly Gln Asp Ala Cys
    530                 535                 540
Gly Ser Asn Ser Trp Asn Met Val Asp Val Asp Leu Pro Pro Asn Lys
545                 550                 555                 560
Asp Val Glu Pro Gly Ile Leu Leu His Gly Leu Lys Pro Trp Thr Gln
                565                 570                 575
Tyr Ala Val Tyr Val Lys Ala Val Thr Leu Thr Met Val Glu Asn Asp
            580                 585                 590
His Ile Arg Gly Ala Lys Ser Glu Ile Leu Tyr Ile Arg Thr Asn Ala
        595                 600                 605
Ser Val Pro Ser Ile Pro Leu Asp Val Leu Ser Ala Ser Asn Ser Ser
    610                 615                 620
Ser Gln Leu Ile Val Lys Trp Asn Pro Pro Ser Leu Pro Asn Gly Asn
625                 630                 635                 640
Leu Ser Tyr Tyr Ile Val Arg Trp Gln Arg Gln Pro Gln Asp Gly Tyr
                645                 650                 655
Leu Tyr Arg His Asn Tyr Cys Ser Lys Asp Lys Ile Pro Ile Arg Lys
            660                 665                 670
Tyr Ala Asp Gly Thr Ile Asp Ile Glu Glu Val Thr Glu Asn Pro Lys
        675                 680                 685
Thr Glu Val Cys Gly Gly Glu Lys Gly Pro Cys Cys Ala Cys Pro Lys
    690                 695                 700
Thr Glu Ala Glu Lys Gln Ala Glu Lys Glu Glu Ala Glu Tyr Arg Lys
705                 710                 715                 720
Val Phe Glu Asn Phe Leu His Asn Ser Ile Phe Val Pro Arg Pro Glu
                725                 730                 735

<210> SEQ ID NO 7
<211> LENGTH: 737
<212> TYPE: PRT
<213> ORGANISM: Artificial Sequence
<220> FEATURE:
<223> OTHER INFORMATION: Synthetic

<400> SEQUENCE: 7

Met Lys Ser Gly Ser Gly Gly Ser Pro Thr Ser Leu Trp Gly Leu
1               5                   10                  15
Leu Phe Leu Ser Ala Ala Leu Ser Leu Trp Pro Thr Ser Gly Glu Ile
                20                  25                  30
Cys Gly Pro Gly Ile Asp Ile Arg Asn Asp Tyr Gln Gln Leu Lys Arg
            35                  40                  45
Leu Glu Asn Cys Thr Val Ile Glu Gly Tyr Leu His Ile Leu Leu Ile
        50                  55                  60
Ser Lys Ala Glu Asp Tyr Arg Ser Tyr Arg Phe Pro Lys Leu Thr Val
65                  70                  75                  80
Ile Thr Glu Tyr Leu Leu Leu Phe Arg Val Ala Gly Leu Glu Ser Leu
                85                  90                  95
Gly Asp Leu Phe Pro Asn Leu Thr Val Ile Arg Gly Trp Lys Leu Phe
            100                 105                 110
Tyr Asn Tyr Ala Leu Val Ile Phe Glu Met Thr Asn Leu Lys Asp Ile
        115                 120                 125
Gly Leu Tyr Asn Leu Arg Asn Ile Thr Arg Gly Ala Ile Arg Ile Glu
    130                 135                 140
Lys Asn Ala Asp Leu Cys Tyr Leu Ser Thr Val Asp Trp Ser Leu Ile
145                 150                 155                 160
```

```
Leu Asp Ala Val Ser Asn Asn Tyr Ile Val Gly Asn Lys Pro Pro Lys
            165                 170                 175

Glu Cys Gly Asp Leu Cys Pro Gly Thr Met Glu Lys Pro Met Cys
            180                 185                 190

Glu Lys Thr Thr Ile Asn Asn Glu Tyr Asn Tyr Arg Cys Trp Thr Thr
            195                 200                 205

Asn Arg Cys Gln Lys Met Cys Pro Ser Thr Cys Gly Lys Arg Ala Cys
            210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Thr Gly Asp Lys Thr His Thr
            485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
            530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
            565                 570                 575
```

```
Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
        595                 600                 605

Lys Ala Lys Gly Gln Pro Arg Glu Pro Gln Val Tyr Thr Leu Pro Pro
    610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
        675                 680                 685

Gln Gln Gly Asn Val Phe Ser Cys Ser Val Met His Glu Ala Leu His
    690                 695                 700

Asn His Tyr Thr Gln Lys Ser Leu Ser Leu Ser Pro Gly Lys Ala Arg
705                 710                 715                 720

Ala Val Phe Glu Asn Phe Leu His Asn Ser Ile Phe Val Pro Arg Pro
                725                 730                 735

Glu

<210> SEQ ID NO 8
<211> LENGTH: 985
<212> TYPE: PRT
<213> ORGANISM: Artificial Sequence
<220> FEATURE:
<223> OTHER INFORMATION: Synthetic

<400> SEQUENCE: 8

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
```

-continued

```
            195                 200                 205
Asn Arg Cys Gln Lys Met Cys Pro Ser Thr Cys Gly Lys Arg Ala Cys
        210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
                245                 250                 255
Ala Gly Val Cys Val Pro Ala Cys Pro Pro Asn Thr Tyr Arg Phe Glu
            260                 265                 270
Gly Trp Arg Cys Val Asp Arg Asp Phe Cys Ala Asn Ile Leu Ser Ala
        275                 280                 285
Glu Ser Ser Asp Ser Glu Gly Phe Val Ile His Asp Gly Glu Cys Met
    290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
                325                 330                 335
Lys Thr Lys Thr Ile Asp Ser Val Thr Ser Ala Gln Met Leu Gln Gly
            340                 345                 350
Cys Thr Ile Phe Lys Gly Asn Leu Leu Ile Asn Ile Arg Arg Gly Asn
        355                 360                 365
Asn Ile Ala Ser Glu Leu Glu Asn Phe Met Gly Leu Ile Glu Val Val
    370                 375                 380
Thr Gly Tyr Val Lys Ile Arg His Ser His Ala Leu Val Ser Leu Ser
385                 390                 395                 400
Phe Leu Lys Asn Leu Arg Leu Ile Leu Gly Glu Glu Gln Leu Glu Gly
                405                 410                 415
Asn Tyr Ser Phe Tyr Val Leu Asp Asn Gln Asn Leu Gln Gln Leu Trp
            420                 425                 430
Asp Trp Asp His Arg Asn Leu Thr Ile Lys Ala Gly Lys Met Tyr Phe
        435                 440                 445
Ala Phe Asn Pro Lys Leu Cys Val Ser Glu Ile Tyr Arg Met Glu Glu
    450                 455                 460
Val Thr Gly Thr Lys Gly Arg Gln Ser Lys Gly Asp Ile Asn Thr Arg
465                 470                 475                 480
Asn Asn Gly Glu Arg Ala Ser Cys Glu Thr Gly Asp Lys Thr His Thr
                485                 490                 495
Cys Pro Pro Cys Pro Ala Pro Glu Leu Leu Gly Gly Pro Ser Val Phe
            500                 505                 510
Leu Phe Pro Pro Lys Pro Lys Asp Thr Leu Met Ile Ser Arg Thr Pro
        515                 520                 525
Glu Val Thr Cys Val Val Val Asp Val Ser His Glu Asp Pro Glu Val
    530                 535                 540
Lys Phe Asn Trp Tyr Val Asp Gly Val Glu Val His Asn Ala Lys Thr
545                 550                 555                 560
Lys Pro Arg Glu Glu Gln Tyr Asn Ser Thr Tyr Arg Val Val Ser Val
                565                 570                 575
Leu Thr Val Leu His Gln Asp Trp Leu Asn Gly Lys Glu Tyr Lys Cys
            580                 585                 590
Lys Val Ser Asn Lys Ala Leu Pro Ala Pro Ile Glu Lys Thr Ile Ser
        595                 600                 605
Lys Ala Lys Gly Gln Pro Arg Glu Pro Gln Val Tyr Thr Leu Pro Pro
    610                 615                 620
```

```
Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
            645                 650                 655

Gln Pro Glu Asn Asn Tyr Lys Thr Thr Pro Pro Val Leu Asp Ser Asp
        660                 665                 670

Gly Ser Phe Phe Leu Tyr Ser Lys Leu Thr Val Asp Lys Ser Arg Trp
    675                 680                 685

Gln Gln Gly Asn Val Phe Ser Cys Ser Val Met His Glu Ala Leu His
690                 695                 700

Asn His Tyr Thr Gln Lys Ser Leu Ser Leu Ser Pro Gly Lys Ala Arg
705                 710                 715                 720

Ala Val Phe Glu Asn Phe Leu His Asn Ser Ile Phe Val Pro Arg Pro
            725                 730                 735

Glu Thr Gly Asp Lys Thr His Thr Cys Pro Pro Cys Pro Ala Pro Glu
        740                 745                 750

Leu Leu Gly Gly Pro Ser Val Phe Leu Phe Pro Pro Lys Pro Lys Asp
    755                 760                 765

Thr Leu Met Ile Ser Arg Thr Pro Glu Val Thr Cys Val Val Val Asp
770                 775                 780

Val Ser His Glu Asp Pro Glu Val Lys Phe Asn Trp Tyr Val Asp Gly
785                 790                 795                 800

Val Glu Val His Asn Ala Lys Thr Lys Pro Arg Glu Glu Gln Tyr Asn
            805                 810                 815

Ser Thr Tyr Arg Val Val Ser Val Leu Thr Val Leu His Gln Asp Trp
        820                 825                 830

Leu Asn Gly Lys Glu Tyr Lys Cys Lys Val Ser Asn Lys Ala Leu Pro
    835                 840                 845

Ala Pro Ile Glu Lys Thr Ile Ser Lys Ala Lys Gly Gln Pro Arg Glu
850                 855                 860

Pro Gln Val Tyr Thr Leu Pro Pro Ser Arg Asp Glu Leu Thr Lys Asn
865                 870                 875                 880

Gln Val Ser Leu Thr Cys Leu Val Lys Gly Phe Tyr Pro Ser Asp Ile
            885                 890                 895

Ala Val Glu Trp Glu Ser Asn Gly Gln Pro Glu Asn Asn Tyr Lys Thr
        900                 905                 910

Thr Pro Pro Val Leu Asp Ser Asp Gly Ser Phe Phe Leu Tyr Ser Lys
    915                 920                 925

Leu Thr Val Asp Lys Ser Arg Trp Gln Gln Gly Asn Val Phe Ser Cys
930                 935                 940

Ser Val Met His Glu Ala Leu His Asn His Tyr Thr Gln Lys Ser Leu
945                 950                 955                 960

Ser Leu Ser Pro Gly Lys Ala Arg Ala Val Phe Glu Asn Phe Leu His
            965                 970                 975

Asn Ser Ile Phe Val Pro Arg Pro Glu
        980                 985

<210> SEQ ID NO 9
<211> LENGTH: 903
<212> TYPE: PRT
<213> ORGANISM: Artificial Sequence
<220> FEATURE:
<223> OTHER INFORMATION: Synthetic

<400> SEQUENCE: 9
```

-continued

```
Met Val Leu Leu Arg Leu Ile Cys Phe Ile Ala Leu Leu Ile Ser Ser
  1               5                  10                  15

Leu Glu Ala Asp Lys Cys Lys Glu Arg Glu Lys Ile Ile Leu Val
          20                  25                  30

Ser Ser Ala Asn Glu Ile Asp Val Arg Pro Cys Pro Leu Asn Pro Asn
          35                  40                  45

Glu His Lys Gly Thr Ile Thr Trp Tyr Lys Asp Asp Ser Lys Thr Pro
      50                  55                  60

Val Ser Thr Glu Gln Ala Ser Arg Ile His Gln His Lys Glu Lys Leu
 65              70                  75                  80

Trp Phe Val Pro Ala Lys Val Glu Asp Ser Gly His Tyr Tyr Cys Val
              85                  90                  95

Val Arg Asn Ser Ser Tyr Cys Leu Arg Ile Lys Ile Ser Ala Lys Phe
             100                 105                 110

Val Glu Asn Glu Pro Asn Leu Cys Tyr Asn Ala Gln Ala Ile Phe Lys
             115                 120                 125

Gln Lys Leu Pro Val Ala Gly Asp Gly Gly Leu Val Cys Pro Tyr Met
     130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
             180                 185                 190

Tyr Thr Cys His Ala Ser Tyr Thr Tyr Leu Gly Lys Gln Tyr Pro Ile
         195                 200                 205

Thr Arg Val Ile Glu Phe Ile Thr Leu Glu Glu Asn Lys Pro Thr Arg
     210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
             260                 265                 270

Leu Gly Glu Asp Tyr Tyr Ser Val Glu Asn Pro Ala Asn Lys Arg Arg
         275                 280                 285

Ser Thr Leu Ile Thr Val Leu Asn Ile Ser Glu Ile Glu Ser Arg Phe
     290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Thr Gly Asp Lys
                325                 330                 335

Thr His Thr Cys Pro Pro Cys Pro Ala Pro Glu Leu Leu Gly Gly Pro
             340                 345                 350

Ser Val Phe Leu Phe Pro Pro Lys Pro Lys Asp Thr Leu Met Ile Ser
         355                 360                 365

Arg Thr Pro Glu Val Thr Cys Val Val Val Asp Val Ser His Glu Asp
     370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415
```

-continued

Val Ser Val Leu Thr Val Leu His Gln Asp Trp Leu Asn Gly Lys Glu
            420                 425                 430

Tyr Lys Cys Lys Val Ser Asn Lys Ala Leu Pro Ala Pro Ile Glu Lys
            435                 440                 445

Thr Ile Ser Lys Ala Lys Gly Gln Pro Arg Glu Pro Gln Val Tyr Thr
            450                 455                 460

Leu Pro Pro Ser Arg Asp Glu Leu Thr Lys Asn Gln Val Ser Leu Thr
465                 470                 475                 480

Cys Leu Val Lys Gly Phe Tyr Pro Ser Asp Ile Ala Val Glu Trp Glu
                485                 490                 495

Ser Asn Gly Gln Pro Glu Asn Asn Tyr Lys Thr Thr Pro Pro Val Leu
            500                 505                 510

Asp Ser Asp Gly Ser Phe Phe Leu Tyr Ser Lys Leu Thr Val Asp Lys
            515                 520                 525

Ser Arg Trp Gln Gln Gly Asn Val Phe Ser Cys Ser Val Met His Glu
530                 535                 540

Ala Leu His Asn His Tyr Thr Gln Lys Ser Leu Ser Leu Ser Pro Gly
545                 550                 555                 560

Lys Ala Arg Ala Ser Glu Arg Cys Asp Asp Trp Gly Leu Asp Thr Met
                565                 570                 575

Arg Gln Ile Gln Val Phe Glu Asp Glu Pro Ala Arg Ile Lys Cys Pro
            580                 585                 590

Leu Phe Glu His Phe Leu Lys Phe Asn Tyr Ser Thr Ala His Ser Ala
            595                 600                 605

Gly Leu Thr Leu Ile Trp Tyr Trp Thr Arg Gln Asp Arg Asp Leu Glu
            610                 615                 620

Glu Pro Ile Asn Phe Arg Leu Pro Glu Asn Arg Ile Ser Lys Glu Lys
625                 630                 635                 640

Asp Val Leu Trp Phe Arg Pro Thr Leu Leu Asn Asp Thr Gly Asn Tyr
                645                 650                 655

Thr Cys Met Leu Arg Asn Thr Thr Tyr Cys Ser Lys Val Ala Phe Pro
            660                 665                 670

Leu Glu Val Val Gln Lys Asp Ser Cys Phe Asn Ser Pro Met Lys Leu
            675                 680                 685

Pro Val His Lys Leu Tyr Ile Glu Tyr Gly Ile Gln Arg Ile Thr Cys
            690                 695                 700

Pro Asn Val Asp Gly Tyr Phe Pro Ser Ser Val Lys Pro Thr Ile Thr
705                 710                 715                 720

Trp Tyr Met Gly Cys Tyr Lys Ile Gln Asn Phe Asn Asn Val Ile Pro
                725                 730                 735

Glu Gly Met Asn Leu Ser Phe Leu Ile Ala Leu Ile Ser Asn Asn Gly
            740                 745                 750

Asn Tyr Thr Cys Val Val Thr Tyr Pro Glu Asn Gly Arg Thr Phe His
            755                 760                 765

Leu Thr Arg Thr Leu Thr Val Lys Val Val Gly Ser Pro Lys Asn Ala
            770                 775                 780

Val Pro Pro Val Ile His Ser Pro Asn Asp His Val Val Tyr Glu Lys
785                 790                 795                 800

Glu Pro Gly Glu Glu Leu Leu Ile Pro Cys Thr Val Tyr Phe Ser Phe
                805                 810                 815

Leu Met Asp Ser Arg Asn Glu Val Trp Trp Thr Ile Asp Gly Lys Lys
            820                 825                 830

Pro Asp Asp Ile Thr Ile Asp Val Thr Ile Asn Glu Ser Ile Ser His

```
                835                 840                 845
Ser Arg Thr Glu Asp Glu Thr Arg Thr Gln Ile Leu Ser Ile Lys Lys
        850                 855                 860

Val Thr Ser Glu Asp Leu Lys Arg Ser Tyr Val Cys His Ala Arg Ser
865                 870                 875                 880

Ala Lys Gly Glu Val Ala Lys Ala Lys Val Lys Gln Lys Val Pro
                885                 890                 895

Ala Pro Arg Tyr Thr Val Glu
            900

<210> SEQ ID NO 10
<211> LENGTH: 1151
<212> TYPE: PRT
<213> ORGANISM: Artificial Sequence
<220> FEATURE:
<223> OTHER INFORMATION: Synthetic

<400> SEQUENCE: 10

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
```

-continued

```
            290                 295                 300
Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Thr Gly Asp Lys
                325                 330                 335

Thr His Thr Cys Pro Cys Pro Ala Pro Glu Leu Leu Gly Gly Pro
                340                 345                 350

Ser Val Phe Leu Phe Pro Pro Lys Pro Lys Asp Thr Leu Met Ile Ser
                355                 360                 365

Arg Thr Pro Glu Val Thr Cys Val Val Val Asp Val Ser His Glu Asp
370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
                405                 410                 415

Val Ser Val Leu Thr Val Leu His Gln Asp Trp Leu Asn Gly Lys Glu
                420                 425                 430

Tyr Lys Cys Lys Val Ser Asn Lys Ala Leu Pro Ala Pro Ile Glu Lys
                435                 440                 445

Thr Ile Ser Lys Ala Lys Gly Gln Pro Arg Glu Pro Gln Val Tyr Thr
450                 455                 460

Leu Pro Pro Ser Arg Asp Glu Leu Thr Lys Asn Gln Val Ser Leu Thr
465                 470                 475                 480

Cys Leu Val Lys Gly Phe Tyr Pro Ser Asp Ile Ala Val Glu Trp Glu
                485                 490                 495

Ser Asn Gly Gln Pro Glu Asn Asn Tyr Lys Thr Thr Pro Pro Val Leu
                500                 505                 510

Asp Ser Asp Gly Ser Phe Phe Leu Tyr Ser Lys Leu Thr Val Asp Lys
                515                 520                 525

Ser Arg Trp Gln Gln Gly Asn Val Phe Ser Cys Ser Val Met His Glu
                530                 535                 540

Ala Leu His Asn His Tyr Thr Gln Lys Ser Leu Ser Leu Ser Pro Gly
545                 550                 555                 560

Lys Ala Arg Ala Val Phe Glu Asn Phe Leu His Asn Ser Ile Phe Val
                565                 570                 575

Pro Arg Pro Glu Thr Gly Asp Lys Thr His Thr Cys Pro Pro Cys Pro
                580                 585                 590

Ala Pro Glu Leu Leu Gly Gly Pro Ser Val Phe Leu Phe Pro Pro Lys
                595                 600                 605

Pro Lys Asp Thr Leu Met Ile Ser Arg Thr Pro Glu Val Thr Cys Val
610                 615                 620

Val Val Asp Val Ser His Glu Asp Pro Glu Val Lys Phe Asn Trp Tyr
625                 630                 635                 640

Val Asp Gly Val Glu Val His Asn Ala Lys Thr Lys Pro Arg Glu Glu
                645                 650                 655

Gln Tyr Asn Ser Thr Tyr Arg Val Val Ser Val Leu Thr Val Leu His
                660                 665                 670

Gln Asp Trp Leu Asn Gly Lys Glu Tyr Lys Cys Lys Val Ser Asn Lys
                675                 680                 685

Ala Leu Pro Ala Pro Ile Glu Lys Thr Ile Ser Lys Ala Lys Gly Gln
                690                 695                 700

Pro Arg Glu Pro Gln Val Tyr Thr Leu Pro Pro Ser Arg Asp Glu Leu
705                 710                 715                 720
```

-continued

```
Thr Lys Asn Gln Val Ser Leu Thr Cys Leu Val Lys Gly Phe Tyr Pro
                725                 730                 735
Ser Asp Ile Ala Val Glu Trp Glu Ser Asn Gly Gln Pro Glu Asn Asn
            740                 745                 750
Tyr Lys Thr Thr Pro Pro Val Leu Asp Ser Asp Gly Ser Phe Phe Leu
        755                 760                 765
Tyr Ser Lys Leu Thr Val Asp Lys Ser Arg Trp Gln Gln Gly Asn Val
770                 775                 780
Phe Ser Cys Ser Val Met His Glu Ala Leu His Asn His Tyr Thr Gln
785                 790                 795                 800
Lys Ser Leu Ser Leu Ser Pro Gly Lys Ala Arg Ala Ser Glu Arg Cys
                805                 810                 815
Asp Asp Trp Gly Leu Asp Thr Met Arg Gln Ile Gln Val Phe Glu Asp
            820                 825                 830
Glu Pro Ala Arg Ile Lys Cys Pro Leu Phe Glu His Phe Leu Lys Phe
        835                 840                 845
Asn Tyr Ser Thr Ala His Ser Ala Gly Leu Thr Leu Ile Trp Tyr Trp
850                 855                 860
Thr Arg Gln Asp Arg Asp Leu Glu Glu Pro Ile Asn Phe Arg Leu Pro
865                 870                 875                 880
Glu Asn Arg Ile Ser Lys Glu Lys Asp Val Leu Trp Phe Arg Pro Thr
                885                 890                 895
Leu Leu Asn Asp Thr Gly Asn Tyr Thr Cys Met Leu Arg Asn Thr Thr
            900                 905                 910
Tyr Cys Ser Lys Val Ala Phe Pro Leu Glu Val Val Gln Lys Asp Ser
        915                 920                 925
Cys Phe Asn Ser Pro Met Lys Leu Pro Val His Lys Leu Tyr Ile Glu
930                 935                 940
Tyr Gly Ile Gln Arg Ile Thr Cys Pro Asn Val Asp Gly Tyr Phe Pro
945                 950                 955                 960
Ser Ser Val Lys Pro Thr Ile Thr Trp Tyr Met Gly Cys Tyr Lys Ile
                965                 970                 975
Gln Asn Phe Asn Asn Val Ile Pro Glu Gly Met Asn Leu Ser Phe Leu
            980                 985                 990
Ile Ala Leu Ile Ser Asn Asn Gly Asn Tyr Thr Cys Val Val Thr Tyr
        995                 1000                1005
Pro Glu Asn Gly Arg Thr Phe His Leu Thr Arg Thr Leu Thr Val Lys
1010                1015                1020
Val Val Gly Ser Pro Lys Asn Ala Val Pro Pro Val Ile His Ser Pro
1025                1030                1035                1040
Asn Asp His Val Val Tyr Glu Lys Glu Pro Gly Glu Glu Leu Leu Ile
                1045                1050                1055
Pro Cys Thr Val Tyr Phe Ser Phe Leu Met Asp Ser Arg Asn Glu Val
            1060                1065                1070
Trp Trp Thr Ile Asp Gly Lys Lys Pro Asp Asp Ile Thr Ile Asp Val
        1075                1080                1085
Thr Ile Asn Glu Ser Ile Ser His Ser Arg Thr Glu Asp Glu Thr Arg
1090                1095                1100
Thr Gln Ile Leu Ser Ile Lys Lys Val Thr Ser Glu Asp Leu Lys Arg
1105                1110                1115                1120
Ser Tyr Val Cys His Ala Arg Ser Ala Lys Gly Glu Val Ala Lys Ala
                1125                1130                1135
```

-continued

```
Ala Lys Val Lys Gln Lys Val Pro Ala Pro Arg Tyr Thr Val Glu
            1140                1145                1150

<210> SEQ ID NO 11
<211> LENGTH: 1149
<212> TYPE: PRT
<213> ORGANISM: Artificial Sequence
<220> FEATURE:
<223> OTHER INFORMATION: Synthetic

<400> SEQUENCE: 11

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350
```

```
Ala Pro Arg Tyr Thr Val Glu Lys Cys Lys Glu Arg Glu Lys Ile
        355                 360                 365
Ile Leu Val Ser Ser Ala Asn Glu Ile Asp Val Arg Pro Cys Pro Leu
    370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
                405                 410                 415
Glu Lys Leu Trp Phe Val Pro Ala Lys Val Glu Asp Ser Gly His Tyr
            420                 425                 430
Tyr Cys Val Val Arg Asn Ser Ser Tyr Cys Leu Arg Ile Lys Ile Ser
        435                 440                 445
Ala Lys Phe Val Glu Asn Glu Pro Asn Leu Cys Tyr Asn Ala Gln Ala
    450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Asn Glu Leu Pro Lys Leu
                485                 490                 495
Gln Trp Tyr Lys Asp Cys Lys Pro Leu Leu Leu Asp Asn Ile His Phe
            500                 505                 510
Ser Gly Val Lys Asp Arg Leu Ile Val Met Asn Val Ala Glu Lys His
        515                 520                 525
Arg Gly Asn Tyr Thr Cys His Ala Ser Tyr Thr Tyr Leu Gly Lys Gln
    530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
    610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
Gly Ile Asp Ala Ala Tyr Ile Gln Leu Ile Tyr Pro Val Thr Asn Thr
            660                 665                 670
Gly Asp Lys Thr His Thr Cys Pro Pro Cys Pro Ala Pro Glu Leu Leu
        675                 680                 685
Gly Gly Pro Ser Val Phe Leu Phe Pro Pro Lys Pro Lys Asp Thr Leu
    690                 695                 700
Met Ile Ser Arg Thr Pro Glu Val Thr Cys Val Val Val Asp Val Ser
705                 710                 715                 720
His Glu Asp Pro Glu Val Lys Phe Asn Trp Tyr Val Asp Gly Val Glu
                725                 730                 735
Val His Asn Ala Lys Thr Lys Pro Arg Glu Glu Gln Tyr Asn Ser Thr
            740                 745                 750
Tyr Arg Val Val Ser Val Leu Thr Val Leu His Gln Asp Trp Leu Asn
        755                 760                 765
Gly Lys Glu Tyr Lys Cys Lys Val Ser Asn Lys Ala Leu Pro Ala Pro
```

-continued

```
            770                 775                 780
Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
                820                 825                 830

Glu Trp Glu Ser Asn Gly Gln Pro Glu Asn Asn Tyr Lys Thr Thr Pro
                835                 840                 845

Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys Ala Arg Ala Val Phe Glu Asn Phe Leu His Asn Ser
                900                 905                 910

Ile Phe Val Pro Arg Pro Glu Ala Arg Ala Asp Lys Thr His Thr Cys
                915                 920                 925

Pro Pro Cys Pro Ala Pro Glu Leu Leu Gly Gly Pro Ser Val Phe Leu
                930                 935                 940

Phe Pro Pro Lys Pro Lys Asp Thr Leu Met Ile Ser Arg Thr Pro Glu
945                 950                 955                 960

Val Thr Cys Val Val Val Asp Val Ser His Glu Asp Pro Glu Val Lys
                965                 970                 975

Phe Asn Trp Tyr Val Asp Gly Val Glu Val His Asn Ala Lys Thr Lys
                980                 985                 990

Pro Arg Glu Glu Gln Tyr Asn Ser Thr Tyr Arg Val Val Ser Val Leu
                995                 1000                1005

Thr Val Leu His Gln Asp Trp Leu Asn Gly Lys Glu Tyr Lys Cys Lys
                1010                1015                1020

Val Ser Asn Lys Ala Leu Pro Ala Pro Ile Glu Lys Thr Ile Ser Lys
1025                1030                1035                1040

Ala Lys Gly Gln Pro Arg Glu Pro Gln Val Tyr Thr Leu Pro Pro Ser
                1045                1050                1055

Arg Asp Glu Leu Thr Lys Asn Gln Val Ser Leu Thr Cys Leu Val Lys
                1060                1065                1070

Gly Phe Tyr Pro Ser Asp Ile Ala Val Glu Trp Glu Ser Asn Gly Gln
                1075                1080                1085

Pro Glu Asn Asn Tyr Lys Thr Thr Pro Pro Val Leu Asp Ser Asp Gly
                1090                1095                1100

Ser Phe Phe Leu Tyr Ser Lys Leu Thr Val Asp Lys Ser Arg Trp Gln
1105                1110                1115                1120

Gln Gly Asn Val Phe Ser Cys Ser Val Met His Glu Ala Leu His Asn
                1125                1130                1135

His Tyr Thr Gln Lys Ser Leu Ser Leu Ser Pro Gly Lys
                1140                1145

<210> SEQ ID NO 12
<211> LENGTH: 708
<212> TYPE: PRT
<213> ORGANISM: Artificial Sequence
<220> FEATURE:
<223> OTHER INFORMATION: Synthetic
```

<400> SEQUENCE: 12

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415
```

-continued

```
Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
        450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
            515                 520                 525

Arg Gly Asn Tyr Thr Cys His Ala Ser Tyr Thr Tyr Leu Gly Lys Gln
        530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
        610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Gly
            660                 665                 670

Pro Gly Gly Glu Gln Lys Leu Ile Ser Glu Glu Asp Leu Gly Gly Glu
            675                 680                 685

Gln Lys Leu Ile Ser Glu Glu Asp Leu Ser Gly His His His His His
        690                 695                 700

His Ser Ser Gly
705

<210> SEQ ID NO 13
<211> LENGTH: 332
<212> TYPE: PRT
<213> ORGANISM: Homo sapiens

<400> SEQUENCE: 13

Met Val Leu Leu Arg Leu Ile Cys Phe Ile Ala Leu Leu Ile Ser Ser
  1               5                  10                  15

Leu Glu Ala Asp Lys Cys Lys Glu Arg Glu Glu Lys Ile Ile Leu Val
             20                  25                  30

Ser Ser Ala Asn Glu Ile Asp Val Arg Pro Cys Pro Leu Asn Pro Asn
         35                  40                  45

Glu His Lys Gly Thr Ile Thr Trp Tyr Lys Asp Asp Ser Lys Thr Pro
     50                  55                  60

Val Ser Thr Glu Gln Ala Ser Arg Ile His Gln His Lys Glu Lys Leu
```

-continued

```
                65                  70                  75                  80
Trp Phe Val Pro Ala Lys Val Glu Asp Ser Gly His Tyr Tyr Cys Val
                    85                  90                  95

Val Arg Asn Ser Ser Tyr Cys Leu Arg Ile Lys Ile Ser Ala Lys Phe
                100                 105                 110

Val Glu Asn Glu Pro Asn Leu Cys Tyr Asn Ala Gln Ala Ile Phe Lys
            115                 120                 125

Gln Lys Leu Pro Val Ala Gly Asp Gly Leu Val Cys Pro Tyr Met
        130                 135                 140

Glu Phe Phe Lys Asn Glu Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
                195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
                260                 265                 270

Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
        290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn
                325                 330

<210> SEQ ID NO 14
<211> LENGTH: 359
<212> TYPE: PRT
<213> ORGANISM: Homo sapiens

<400> SEQUENCE: 14

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110
```

```
Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
    275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu
        355

<210> SEQ ID NO 15
<211> LENGTH: 609
<212> TYPE: PRT
<213> ORGANISM: Artificial Sequence
<220> FEATURE:
<223> OTHER INFORMATION: Synthetic

<400> SEQUENCE: 15

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110
```

```
Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
        130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
                180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
                340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr Ser Gly Asp Lys
        370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
        420                 425                 430

Pro Glu Val Lys Phe Asn Trp Tyr Val Asp Gly Val Glu Val His Asn
        435                 440                 445

Ala Lys Thr Lys Pro Arg Glu Glu Gln Tyr Asn Ser Thr Tyr Arg Val
        450                 455                 460

Val Ser Val Leu Thr Val Leu His Gln Asp Trp Leu Asn Gly Lys Glu
465                 470                 475                 480

Tyr Lys Cys Lys Val Ser Asn Lys Ala Leu Pro Ala Pro Ile Glu Lys
                485                 490                 495

Thr Ile Ser Lys Ala Lys Gly Gln Pro Arg Glu Pro Gln Val Tyr Thr
        500                 505                 510

Leu Pro Pro Ser Arg Asp Glu Leu Thr Lys Asn Gln Val Ser Leu Thr
        515                 520                 525

Cys Leu Val Lys Gly Phe Tyr Pro Ser Asp Ile Ala Val Glu Trp Glu
```

```
                    530                 535                 540
Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
            580                 585                 590

Ala Leu His Asn His Tyr Thr Gln Lys Ser Leu Ser Leu Ser Pro Gly
        595                 600                 605

Lys

<210> SEQ ID NO 16
<211> LENGTH: 858
<212> TYPE: PRT
<213> ORGANISM: Artificial Sequence
<220> FEATURE:
<223> OTHER INFORMATION: Synthetic

<400> SEQUENCE: 16

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285
```

-continued

```
Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
        340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr Thr Gly Asp Lys
    370                 375                 380

Thr His Thr Cys Pro Pro Cys Pro Ala Pro Glu Leu Leu Gly Gly Pro
385                 390                 395                 400

Ser Val Phe Leu Phe Pro Pro Lys Pro Lys Asp Thr Leu Met Ile Ser
                405                 410                 415

Arg Thr Pro Glu Val Thr Cys Val Val Val Asp Val Ser His Glu Asp
        420                 425                 430

Pro Glu Val Lys Phe Asn Trp Tyr Val Asp Gly Val Glu Val His Asn
            435                 440                 445

Ala Lys Thr Lys Pro Arg Glu Glu Gln Tyr Asn Ser Thr Tyr Arg Val
    450                 455                 460

Val Ser Val Leu Thr Val Leu His Gln Asp Trp Leu Asn Gly Lys Glu
465                 470                 475                 480

Tyr Lys Cys Lys Val Ser Asn Lys Ala Leu Pro Ala Pro Ile Glu Lys
                485                 490                 495

Thr Ile Ser Lys Ala Lys Gly Gln Pro Arg Glu Pro Gln Val Tyr Thr
        500                 505                 510

Leu Pro Pro Ser Arg Asp Glu Leu Thr Lys Asn Gln Val Ser Leu Thr
            515                 520                 525

Cys Leu Val Lys Gly Phe Tyr Pro Ser Asp Ile Ala Val Glu Trp Glu
    530                 535                 540

Ser Asn Gly Gln Pro Glu Asn Asn Tyr Lys Thr Thr Pro Pro Val Leu
545                 550                 555                 560

Asp Ser Asp Gly Ser Phe Phe Leu Tyr Ser Lys Leu Thr Val Asp Lys
                565                 570                 575

Ser Arg Trp Gln Gln Gly Asn Val Phe Ser Cys Ser Val Met His Glu
        580                 585                 590

Ala Leu His Asn His Tyr Thr Gln Lys Ser Leu Ser Leu Ser Pro Gly
            595                 600                 605

Lys Ala Arg Ala Val Phe Glu Asn Phe Leu His Asn Ser Ile Phe Val
    610                 615                 620

Pro Arg Pro Glu Ala Arg Ala Asp Lys Thr His Thr Cys Pro Pro Cys
625                 630                 635                 640

Pro Ala Pro Glu Leu Leu Gly Gly Pro Ser Val Phe Leu Phe Pro Pro
                645                 650                 655

Lys Pro Lys Asp Thr Leu Met Ile Ser Arg Thr Pro Glu Val Thr Cys
        660                 665                 670

Val Val Asp Val Ser His Glu Asp Pro Glu Val Lys Phe Asn Trp
            675                 680                 685

Tyr Val Asp Gly Val Glu Val His Asn Ala Lys Thr Lys Pro Arg Glu
    690                 695                 700
```

```
Glu Gln Tyr Asn Ser Thr Tyr Arg Val Val Ser Val Leu Thr Val Leu
705                 710                 715                 720

His Gln Asp Trp Leu Asn Gly Lys Glu Tyr Lys Cys Lys Val Ser Asn
            725                 730                 735

Lys Ala Leu Pro Ala Pro Ile Glu Lys Thr Ile Ser Lys Ala Lys Gly
        740                 745                 750

Gln Pro Arg Glu Pro Gln Val Tyr Thr Leu Pro Pro Ser Arg Asp Glu
    755                 760                 765

Leu Thr Lys Asn Gln Val Ser Leu Thr Cys Leu Val Lys Gly Phe Tyr
770                 775                 780

Pro Ser Asp Ile Ala Val Glu Trp Glu Ser Asn Gly Gln Pro Glu Asn
785                 790                 795                 800

Asn Tyr Lys Thr Thr Pro Pro Val Leu Asp Ser Asp Gly Ser Phe Phe
            805                 810                 815

Leu Tyr Ser Lys Leu Thr Val Asp Lys Ser Arg Trp Gln Gln Gly Asn
        820                 825                 830

Val Phe Ser Cys Ser Val Met His Glu Ala Leu His Asn His Tyr Thr
    835                 840                 845

Gln Lys Ser Leu Ser Leu Ser Pro Gly Lys
    850                 855

<210> SEQ ID NO 17
<211> LENGTH: 900
<212> TYPE: PRT
<213> ORGANISM: Artificial Sequence
<220> FEATURE:
<223> OTHER INFORMATION: Synthetic

<400> SEQUENCE: 17

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205
```

```
Asn Tyr Thr Cys Val Val Thr Tyr Pro Glu Asn Gly Arg Thr Phe His
210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
                260                 265                 270
Leu Met Asp Ser Arg Asn Glu Val Trp Trp Thr Ile Asp Gly Lys Lys
            275                 280                 285
Pro Asp Asp Ile Thr Ile Asp Val Thr Ile Asn Glu Ser Ile Ser His
        290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
                340                 345                 350
Ala Pro Arg Tyr Thr Val Glu Lys Cys Lys Glu Arg Glu Glu Lys Ile
                355                 360                 365
Ile Leu Val Ser Ser Ala Asn Glu Ile Asp Val Arg Pro Cys Pro Leu
        370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
                405                 410                 415
Glu Lys Leu Trp Phe Val Pro Ala Lys Val Glu Asp Ser Gly His Tyr
            420                 425                 430
Tyr Cys Val Val Arg Asn Ser Ser Tyr Cys Leu Arg Ile Lys Ile Ser
        435                 440                 445
Ala Lys Phe Val Glu Asn Glu Pro Asn Leu Cys Tyr Asn Ala Gln Ala
    450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Asn Glu Leu Pro Lys Leu
                485                 490                 495
Gln Trp Tyr Lys Asp Cys Lys Pro Leu Leu Leu Asp Asn Ile His Phe
            500                 505                 510
Ser Gly Val Lys Asp Arg Leu Ile Val Met Asn Val Ala Glu Lys His
        515                 520                 525
Arg Gly Asn Tyr Thr Cys His Ala Ser Tyr Thr Tyr Leu Gly Lys Gln
530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
            580                 585                 590
Ser Asp Ile Ala Tyr Trp Lys Trp Asn Gly Ser Val Ile Asp Glu Asp
        595                 600                 605
Asp Pro Val Leu Gly Glu Asp Tyr Tyr Ser Val Glu Asn Pro Ala Asn
        610                 615                 620
Lys Arg Arg Ser Thr Leu Ile Thr Val Leu Asn Ile Ser Glu Ile Glu
```

-continued

```
625                 630                 635                 640
Ser Arg Phe Tyr Lys His Pro Phe Thr Cys Phe Ala Lys Asn Thr His
                    645                 650                 655

Gly Ile Asp Ala Ala Tyr Ile Gln Leu Ile Tyr Pro Val Thr Asn Ser
                    660                 665                 670

Gly Asp Lys Thr His Thr Cys Pro Pro Cys Pro Ala Pro Glu Leu Leu
                    675                 680                 685

Gly Gly Pro Ser Val Phe Leu Phe Pro Pro Lys Pro Lys Asp Thr Leu
            690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                    725                 730                 735

Val His Asn Ala Lys Thr Lys Pro Arg Glu Glu Gln Tyr Asn Ser Thr
                    740                 745                 750

Tyr Arg Val Val Ser Val Leu Thr Val Leu His Gln Asp Trp Leu Asn
                    755                 760                 765

Gly Lys Glu Tyr Lys Cys Lys Val Ser Asn Lys Ala Leu Pro Ala Pro
            770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                    805                 810                 815

Ser Leu Thr Cys Leu Val Lys Gly Phe Tyr Pro Ser Asp Ile Ala Val
                    820                 825                 830

Glu Trp Glu Ser Asn Gly Gln Pro Glu Asn Asn Tyr Lys Thr Thr Pro
            835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                    885                 890                 895

Ser Pro Gly Lys
            900
```